United States Patent [19]

Denzel et al.

[11] 4,223,142
[45] Sep. 16, 1980

[54] AMINO DERIVATIVES OF PYRIDO(2,3-d)PYRIDAZINE CARBOXYLIC ACIDS AND ESTERS

[75] Inventors: Theodor Denzel, Regensburg; Hans Hoehn, Tegernheim, both of Fed. Rep. of Germany

[73] Assignee: E. R. Squibb & Sons, Inc., Princeton, N.J.

[21] Appl. No.: 696,615

[22] Filed: Jun. 16, 1976

Related U.S. Application Data

[63] Continuation-in-part of Ser. No. 252,775, May 12, 1972, abandoned.

[51] Int. Cl.³ .................... C07D 471/04; A61K 31/50
[52] U.S. Cl. .................................. 544/236; 546/193; 546/281; 546/286; 544/238; 544/365
[58] Field of Search .................. 260/268 BC, 256.5 R, 260/250 AC; 544/236

[56] References Cited

PUBLICATIONS

Denzel et al., CA 80, 37145d (1973).

Primary Examiner—Mark L. Berch
Attorney, Agent, or Firm—Lawrence S. Levinson

[57] ABSTRACT

The new amino derivatives of pyrido[2,3-d]pyridazine carboxylic esters and acids have the general formula

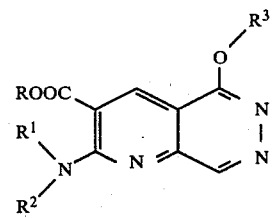

They are useful as analgesic, anti-inflammatory agents and central nervous system depressants. In addition, this type of compound increases the intracellular concentration of adenosine-3',5'-cyclic monophosphate.

14 Claims, No Drawings

AMINO DERIVATIVES OF PYRIDO(2,3-d)PYRIDAZINE CARBOXYLIC ACIDS AND ESTERS

PRIOR APPLICATIONS

This application is a continuation-in-part of application Ser. No. 252,775, filed May 12, 1972 and now abandoned.

SUMMARY OF THE INVENTION

This invention relates to new amino derivatives of pyrido[2,3-d]-pyridazines-3-carboxylic esters and acids as well as their salts. These new compounds have the formula

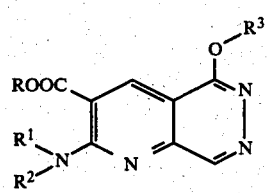

and, when $R^3$ is hydrogen, include the tautomeric form of the formula

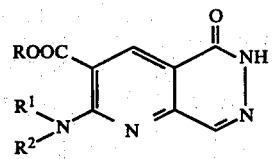

The symbols have the following meanings in formula I and throughout this specification: R is hydrogen or lower alkyl. The basic nitrogen group

is an acyclic amino moiety wherein $R^1$ and $R^2$ each is hydrogen, lower alkyl, phenyl, substituted phenyl (i.e. the phenyl ring contains one or two simple substituents including lower alkyl, trifluoromethyl or carboxy, preferably only one of the latter two substituents), phenyl-lower alkylene or di-lower alkylamino-lower alkylene (preferably only one of the last mentioned group). This basic group may also form a heterocyclic of 5 or 6 members in which an additional nitrogen may be present, i.e., pyrrolidino, piperidino, pyrazolyl, pyrimidinyl, pyridazinyl, dihydropyridazinyl or piperazinyl radicals, each of which may also bear as a substituent a hydroxy-lower alkyl group or one or two lower alkyl groups. The lower alkyl and lower alkylene groups in any of the foregoing radicals are straight or branched chain hydrocarbon groups of up to seven carbon atoms like methyl, ethyl, propyl, isopropyl, t-butyl and the like. $R^3$ is hydrogen or lower alkyl. The products of the examples, which are representative of the various compounds of this invention, constitute preferred embodiments. Especially preferred compounds of formula I are those wherein R is hydrogen or lower alkyl, especially ethyl, R' is ethyl, propyl or butyl, $R^2$ is hydrogen, $R^3$ is hydrogen, methyl, ethyl or isopentyl.

DETAILED DESCRIPTION OF THE INVENTION

The new compounds of formula I are formed by the following series of reactions. The symbols in the structural formulas have the same meaning as previously described.

An alkoxymethylenemalonic acid ester of the formula

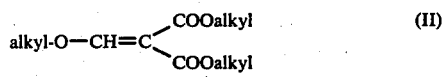

is made to react with a β-amino-crotonic-acid nitrile of the formula

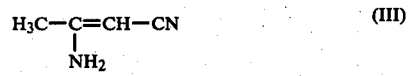

at about 140°–150°, while the alcohol formed is distilled off. A product of the formula

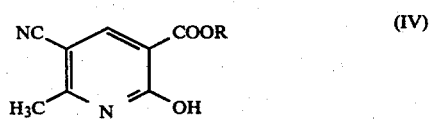

is formed. This compound is refluxed for several hours with a phosphorous halide, like phosphorous oxychloride, to obtain the intermediate of the formula

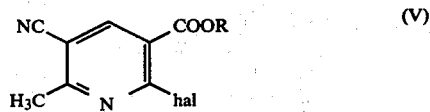

wherein hal is halogen.

This intermediate is then made to react with the appropriate primary or secondary amine of the formula

to produce a compound of the formula

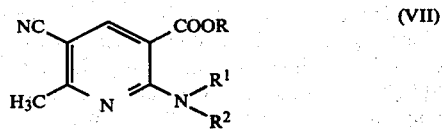

This reaction is effected by stirring the reactants at room temperature or elevated temperatures.

The compound of formula VII is then oxidized with an appropriate oxidation agent like selenium dioxide to form a compound of the formula

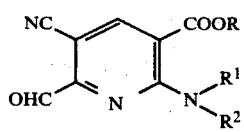

By the reaction of compounds of formula VIII with hydrazine or hydrazine hydrate, the hydrazone of formula

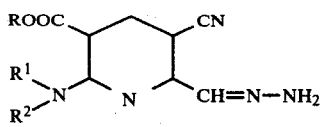

is formed. Compound of formula

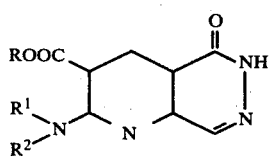

are now produced by treatment of compounds of formula IX with acetic acid, pyridine, or sodium alkoxides. This compound is then transformed to the compounds of formula

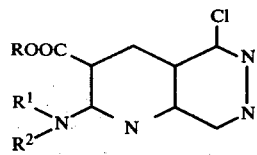

with a chlorine in the 5-position, on treatment with phosphorous oxychloride.

Compounds of formula I are now obtained by reaction of compounds of formula XI with the appropriate alkalimetal alkoxides.

The ester may be hydrolyzed, e.g., with a dilute alkali hydroxide like sodium hydroxide to obtain the acid, i.e., wherein R is hydrogen. The compounds of formula I form salts which are also part of this invention. The salts include acid-addition salts, particularly the non-toxic, physiologically acceptable members. The bases of formula I form salts by reaction with a variety of inorganic and organic acids providing acid addition salts including, for example, hydrohalides like hydrochloride, hydrobromide, etc., sulfate, nitrate, phosphate, oxalate, tartrate, malate, citrate, acetate, ascorbate, succinate, benzenesulfonate, toluenesulfonate, etc. The acid addition salts frequently provide a convenient menas for isolating a particular product, e.g., by forming and precipitating one salt in an approptriate medium in which it is insoluble, then after separating the salt, neutralizing with a base to obtain a free base of formula I. Other salts may then be formed from the free base by reaction with an equivalent of the acid forming the desired salt.

The new compounds of this invention have analgesic and anti-inflammatory properties and are useful, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats. The active substance may be utilized in compositions such as tablets, capsules, solutions or suspensions containing up to about 300 mg per unit of dosage of a compound or mixture of compounds of formula I or physiologically acceptable acid addition or quaternary ammonium salt thereof. They may be compounded in conventional manner with a physiologically acceptable vehicle or carrier, excipient, binder, preservative, stabilizer, flavor, etc. as called for by accepted pharmaceutical practice. Topical preparations containing about 0.01 to 3% by weight of active substance in a lotion, salve or cream may also be used.

The new compounds of this invention are also central nervous system depressants and may be used as tranquilizers or ataractic agents for the relief of anxiety and tension states, for example, in mice, cats, rats, dogs and other mammalian species, in the same manner as chlordiazepoxide. For this purpose a compound or mixture of compounds of formula I, or non-toxic, physiologically acceptable acid addition salt thereof, may be administered orally or parenterally in a conventional dosage form such as tablet, capsule, injectable or the like. A single dose, or preferably 2 to 4 divided daily doses, provided on a basis of about 1 to 50 mg per kilogram per day, preferably about 2 to 15 mg/kg/day, is appropriate. These may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice.

The new compounds in addition increase the intracellular concentration of adenosine-3',5'-cyclic monophosphate, and thus by the administration of about 1 to 100 mg/kg/day, preferably about 10 to 50 mg/kg, in single or two to four divided doses in conventional oral or parenteral dosage forms such as those described above may be used to alleviate the symptoms of asthma.

The following examples are illustrative of the invention.

EXAMPLE 1

2-Butylamino-5-hydroxy-pyrido[2,3-d]pyridazine-3-carboxylic acid, ethyl ester (a) 5-Cyano-2-hydroxy-6-methyl-3-pyridine-carboxylic acid, ethyl ester 432 g of ethoxymethylenemalonic acid, diethyl ester (2 mol) and 164 g of 3-aminocrotonic acid nitrile are heated together for 2 hrs. at 140°–150° C. After standing over night, the precipitated 5-cyano-2-hydroxy-6-methyl-5-pyridine-carboxylic acid, ethyl ester is filtered off, washed with ice-cold methanol. Yield 300 g (73%); m.p. 212°–213° C. (methanol).

(b) 2-Chloro-5-cyano-6-methyl-3-pyridine-carboxylic acid, ethyl ester 200 g of 5-cyano-2-hydroxy-6-methyl-3-pyridine-carboxylic acid, ethyl ester (1 mol) are refluxed with stirring in 750 ml of phosphorous oxychloride for 5 hours. The excess of phosphorous oxychloride is removed in vacuo and the residue poured in 1 kg of ice. 2-chloro-5-cyano-6-methyl-3-pyridine-carboxylic acid, ethyl ester crystallizes and is filtered off. Yield 170 g (76%); m.p. 43°–45° C. (petrol ether).

(c)
2-Butylamino-5-cyano-6-methyl-3-pyridine-carboxylic acid, ethyl ester 112 g of 2-chloro-5-cyano-6-methyl-3-pyridine-carboxylic acid, ethyl ester (0.5 mol) are dissolved in 300 ml of alcohol and 73 g of n-butylamine are dropped in at reflux temperature with stirring. After the addition is completed, the mixture is refluxed for an additional hour and then poured onto ice. 2-butylamino-5-cyano-6-methyl-3-pyridine-carboxylic acid, ethyl ester precipitates. Yield 116 g (89%); m.p. 61°–63° C. (petrol ether).

(d)
2-Butylamino-5-cyano-6-formyl-3-pyridine-carboxylic acid, ethyl ester 130.5 g of 2-butylamino-5-cyano-6-methyl-3-pyridine-carboxylic acid, ethyl ester (0.5 mol) are dissolved in 400 ml of diethyleneglycoldimethyl ether. 61.1 g of selenium dioxide are added and the mistrue is heated at reflux temperature for 1 hour. The mixture is filtered hot and evaporated to dryness. The resulting yellow oil of 2-butylamino-5-cyano-6-formyl-3-pyridine-carboxylic acid, ethyl ester is crystallized with diethyl ether. Yield 95 g (69%); m.p. 81°–83° C. (methanol).

(e)
2-Butylamino-5-cyano-6-methylidene-hydrazino-3-pyridine-carboxylic acid, ethyl ester 27.5 g of 2-butylamino-5-cyano-6-formyl-3-pyridine-carboxylic acid, ethyl ester (0.1 mol) are dissolved in 100 ml methanol. 7.5 g of 96% hydrazinehydrate are added dropwise with stirring and after the addition is completed, the mixture is allowed to stand over night. The hydrazone crystallizes and is filtered off. Yield 21 g (73%); m.p. 130°–132° C. (methanol).

(f)
2-Butylamino-5-hydroxy-pyrido[2,3-d]pyrazine-3-carboxylic acid, ethyl ester 2.9 g of the hydrazone of step (e) (0.01 mol) are refluxed for 1 hour in 10 ml of acetic acid. 2-butylamino-5-hydroxy-pyrido[2,3-d]pyrazine-3-carboxylic acid, ethyl ester crystallizes on cooling. Yield 2.2 g (76%); m.p. 203°–204° C.

EXAMPLE 2
2-Butylamino-5-ethoxy-pyrido[2,3-d]pyridazine-3-carboxylic acid, ethyl ester

(a)
2-Butylamino-5-chloro-pyrido[2,3-d]pyridazine-3-carboxylic acid, ethyl ester 5.8 g of 2-butylamino-5-hydroxy-pyrido[2,3-d]pyridazine-3-carboxylic acid, ethyl ester (0.02 mol) are treated with 20 ml of phosphorous oxychloride for 5 days at room temperature with permanent stirring. The excess of phosphorous oxychloride in distilled off in vacuo and the remaining residue is extracted with 20 ml of hot ethyl acetate. 2-butylamino-5-chloro-pyrido[2,3-d]pyridazine-3-carboxylic acid, ethyl ester crystallizes on cooling. Yield 5.5 g (83%); m.p. 126.7° C. (ligroin).

(b)
2-Butylamino-5-ethoxy-pyrido[2,3-d]pyridazine-3-carboxylic acid, ethyl ester 5.5 g of 2-butylamino-5-chloro-pyrido[2,3-d]pyridazine-3-carboxylic acid, ethyl ester are refluxed in 10 ml of alcohol for 1 hour. The alcohol is cooled to about 0° and the 2-butylamino-5-ethoxy-pyrido[2,3-d]pyridazine-3-carboxylic acid, ethyl ester precipitates. Yield 4.2 g (79%); m.p. 98°–99° C. (ligroin).

EXAMPLE 3
5-Hydroxy-2-[[3-(trifluormethyl)phenyl]amino]-pyrido[2,3-d]pyridazine-3-carboxylic acid, ethyl ester

(a)
5-Cyano-6-methyl-2-[[3-(trifluormethyl)phenyl]amino]-3-pyridine-carboxylic acid, ethyl ester 56 g of 2-chloro-5-cyano-6-methyl-3-pyridine-carboxylic acid, ethyl ester (0.25 mol) of Example 2 (b) are dissolved in 200 ml of alcohol. 30 g of triethylamine are added and the solution is heated at 80° C. with stirring. Now 34 g of 3-trifluormethylaniline are added and heating is continued for 5 hours. The solution is poured onto ice and the precipitated title compound filtered off. Yield 70 g (80%); m.p. 149°–151° C. (methanol).

(b)
5-Cyano-6-formyl-2-[[3-(trifluormethyl)phenyl]amino]-3-pyridine-carboxylic acid, ethyl ester 69.8 g of 5-cyano-6-methyl-2-[[3-(trifluormethyl)phenyl]amino]-3-pyridine-carboxylic acid, ethyl ester (0.2 mol) are dissolved in 400 ml of diethyleneglycoldimethyl ether. After addition of 24.2 g of selenium dioxide, the mixture is heated at 160° with stirring for 2 hrs. The selenium is filtered off and the filtrate evaporated. The resulting yellow title compound is recrystalized from butanol. Yield 56 g (77%); m.p. 183°–185° C.

(c)
5-Cyano-6-methylidene-hydrazino-2-[[3-(trifluormethyl)phenyl]-amino]-3-pyridine-carboxylic acid, ethyl ester 36.3 g of 5-cyano-6-formyl-2-[[3-(trifluormethyl)phenyl]amino]-3-pyridine-carboxylic acid, ethyl ester (0.1 mol) are suspended in 200 ml of methanol. 7.5 g of hydrazinhydrate are added and the mixture is allowed to stand over night, and then the hydrazone is filtered off. Yield 25 g (66%); m.p. 173°–175° C. (butanol).

5-Hydroxy-2-[[3-(trifluormethyl)phenyl]amino]-pyrido(2,3-d]-pyridazine-3-carboxylic acid, ethyl ester 3.7 g of the hydrazone of step (c) are stirred in 10 ml of acetic acid at room temperature over night. The precipitated 5-hydroxy-2-[[3-(trifluormethyl)phenyl]amino]pyrido[2,3-d]pyridazine-3-carboxylic acid, ethyl ester is filtered off. Yield 3.1 g (81%); m.p. 249°–250° C. (DMF).

EXAMPLE 4
5-Hydroxy-2-phenylamino-pyrido[2,3-d]pyridazine-3-carboxylic acid, ethyl ester

(a)
5-Cyano-6-methyl-2-phenylamino-3-pyridine-carboxylic acid, ethyl ester When in Example 3 (a) trifluormethylaniline is replaced by aniline, 5-cyano-6-methyl-2-phenylamino-3-pyridine-carboxylic acid, ethyl ester is obtained. Yield 75%; m.p. 133°–135° C. (methanol).

(b)

5-Cyano-6-formyl-2-phenylamino-3-pyridine-carboxylic acid, ethyl ester

When 5-cyano-6-methyl-2-phenylamino-3-pyridine-carboxylic acid, ethyl ester is processed as described for 5-cyano-6-methyl-2-[[3-(trifluormethyl)phenyl]amino]-3-pyridine-carboxylic acid, ethyl ester in Example 3 (b), 5-cyano-6-formyl-2-phenylamino-3-pyridine-carboxylic acid, ethyl ester is obtained. Yield 78%; m.p. 165°–167° C. (methanol).

(c)

5-Cyano-6-methylidene-hydrazino-2-phenylamino-3-pyridine-carboxylic acid, ethyl ester Treatment of 5-cyano-6-formyl-2-phenylamino-3-pyridine-carboxylic acid, ethyl ester with hydrazine hydrate, according to the procedure of Example 3 (c) results in the formation of 5-cyano-6-methylidene-hydrazino-2-phenylamino-3-pyridine-carboxylic acid, ethyl ester. Yield 68%; m.p. 174°–176° C. (butanol).

(d)

5-Hydroxy-2-phenylamino-pyrido[2,3-d]pyridazine-3-carboxylic acid, ethyl ester 3.1 g of 5-cyano-6-methylidene-hydrazino-2-phenylamino-3-pyridine-carboxylic acid, ethyl ester (0.01 mol) are stirred in 10 ml of acetic acid over night. The precipitated title compound is filtered off and recrystallized from butyl alcohol. Yield 2.4 g (77%): m.p. 257°–260° C.

EXAMPLE 5

5-Hydroxy-2-piperidino-pyrido[2,3-d]pyridazine-3-carboxylic acid, ethyl ester (a)

5-Cyano-6-methyl-2-piperidino-3-pyridine-carboxylic acid, ethyl ester

When in Example 1 (c) n-butylamine is replaced by piperidine, 5-cyano-6-methyl-2-piperidino-3-pyridine-carboxylic acid, ethyl ester is obtained. Yield 78%; m.p. 72°–74° C. (petrol ether).

(b)

5-Cyano-6-formyl-2-piperidinyl-3-pyridine-carboxylic acid, ethyl ester 27 g of 5-cyano-6-methyl-2-piperidinyl-3-pyridine-carboxylic acid, ethyl ester (0.1 mol) and 12.2 g selenium dioxide (0.11 mol) are refluxed together in diethyleneglycoldimethyl ether with stirring for 1.5 hours. The solvent is distilled off in vacuo and the oily residue crystallized with diethyl ether. Yield 19 g (66%); m.p. 62°–64° C. (ether).

(c)

5-Cyano-6-methylidene-hydrazino-2-piperidinyl-3-pyridine-carboxylic acid, ethyl ester 28.7 g of 5-cyano-6-formyl-2-piperidinyl-3-pyridine-carboxylic acid, ethyl ester (0.1 mol) are dissolved in 100 ml of methanol. 5.5 g of hydrazine hydrate are added and the solution is stirred at room temperature over night. The title compound is filtered off and recrystallized from methanol. Yield 20.5 g (68%); m.p. 168°–170° C.

(d)

5-Hydroxy-2-piperidinyl-pyrido[2,3-d]pyridazine-3-carboxylic acid, ethyl ester 3.01 g of 5-cyano-6-methylidene-hydrazino-2-piperidinyl-3-pyridine-carboxylic acid, ethyl ester (0.01 mol) are added to a solution of 0.22 g of sodium in 30 ml of alcohol. The mixture is refluxed for 30 min., acidified with acetic acid and then 10 ml of water are added. 5-hydroxy-2-piperidinyl-pyrido[2,3-d]-pyridazine-3-carboxylic acid, ethyl ester precipitates. Yield 2 g (66%); m.p. 178°–179° C. (methanol).

EXAMPLE 6

2-Diethylamino-5-hydroxy-pyrido[2,3-d]pyridazine-3-carboxylic acid, ethyl ester

When in Example 1(c) n-butylamine is replaced by diethylamine, 5-cyano-2-diethylamino-6-methyl-3-pyridine-carboxylic acid, ethyl ester is obtained. This compound is processed as described in Examples 1(d) and 1(e). By this procedure 5-cyano-2-diethylamino-6-methylidene-hydrazino-3-pyridine-carboxylic acid, ethyl ester is formed. m.p. 138°–140° C.

2.9 g of 5-cyano-2-diethylamino-6-methylidene-hydrazino-3-pyridine-carboxylic acid, ethyl ester are dissolved in 10 ml of diethyleneglycoldimethyl ether and heated with stirring for 30 min. at 140° C. The solvent is removed in vacuo and the crystalline residue of 2-diethylamino-5-hydroxy-pyrido[2,3-d]pyridazine-3-carboxylic acid, ethyl ester recrystallizes from methanol. Yield 2.1 g (72%); m.p. 105°–107° C.

EXAMPLE 7

5-Hydroxy-2-methylamino-pyrido[2,3-d]pyridazine-3-carboxylic acid, ethyl ester

When in Example 1(c) n-butylamine is replaced by methylamine, 5-cyano-6-methyl-2-methylamino-3-pyridine-carboxylic acid, ethyl ester is obtained. Yield 85%; m.p. 103°–105° C. (methanol).

This compound is processed through the oxidation step as described in Example 1(d), yielding 5-cyano-6-formyl-2-methylamino-3-pyridine-carboxylic acid, ethyl ester (m.p. 137°–139° C.), the reaction with hydrazine comprising 5-cyano-2-methylamino-6-methylidene-hydrazino-3-pyridine-carboxylic acid, ethyl ester (m.p. 174°–176° C.), and the following ring closure to give 5-hydroxy-2-methylamino-pyrido[2,3-d]pyridazine-3-carboxylic acid, ethyl ester. Yield (67%); m.p. 290°–292° C. (butanol).

EXAMPLE 8

5-Hydroxy-2-[(1-methylpropyl)amino]pyrido[2,3-d]pyridazine-3-carboxylic acid, ethyl ester (a)

5-Cyano-6-methyl-2-[(1-methylpropyl)amino]-3-pyridine-carboxylic acid, ethyl ester 22.4 g of 2-chloro-5-cyano-6-methyl-3-pyridine-carboxylic acid, ethyl ester (1 mol) of Example 1(b) are treated in 100 ml of ethanol with 15 g sec. butylamine at reflux temperature with stirring. After the addition of the amine is completed, the solution is poured into 200 ml of cold water, and the amino compound is filtered off. Yield 22 g (84%); m.p. 55°–57° C.

(b)
5-Cyano-6-formyl-2-[(1-methylpropyl)amino]-3-pyridine-carboxylic acid, ethyl ester 26.1 g of 5-cyano-6-methyl-2-[(1-methylpropyl)amino]-3-pyridine-carboxylic acid, ethyl ester (0.1 mol) and 13 g of selenium dioxide are refluxed together in dioxane for 24 hours. After this time the selenium is filtered off and the solvent removed in vacuo. The resulting oily residue is crystallized with ether. Yield 19 g (69%); m.p. 37°–38° C. (methanol).

(c)
5-Cyano-6-methylidene-hydrazino-2-[(1-methylpropyl)amino]-3-pyridine-carboxylic acid, ethyl ester 2.8 g of 5-cyano-6-formyl-2-[(1-methylpropyl)amino]-3-pyridine-carboxylic acid, ethyl ester (0.01 mol) are dissolved in 10 ml of methanol and 1 g of hydrazine hydrate is added with stirring. After standing over night the title compound precipitates. Yield 2.1 g (73%); m.p. 120°–121° C. (methanol).

(d)
5-Hydroxy-2-[(1-methylpropyl)amino]pyrido[2,3-d]pyridazine-3-carboxylic acid, ethyl ester 2.9 g of the hydrazone of step (c) are added to 5 ml of acetic acid and the mixture is stirred at room temperature for 72 hours. The crystallized 5-hydroxy-2-[(1-methylpropyl)amino]pyrido[2,3-d]-pyridazine-3-carboxylic acid, ethyl ester is filtered off and recrystallized from butyl alcohol. Yield 2.1 g (72%); m.p. 184°–185° C.

EXAMPLE 9
5-Hydroxy-2-[(1-methylethyl)amino]pyrido[2,3-d]pyridazine-3-carboxylic acid, ethyl ester When in Example 1(c) butylamine is replaced by sec. propylamine, 5-cyano-6-methyl-2-[(1-methylethyl)amino]-3-pyridine-carboxylic acid, ethyl ester is obtained. (Yield 85%; m.p. 59°–61° C. (petrol ether)). This compound is processed as described in Examples 1(d) through 1(f) via the selenium dioxide oxidation and the reaction with hydrazine followed by the ring closure step, providing 5-hydroxy-2-[(1-methylethyl)amino]-pyrido[2,3-d]pyridazine-3-carboxylic acid, ethyl ester; m.p. 219°–220° C.

The following additional products are obtained by the procedure of Example 2:

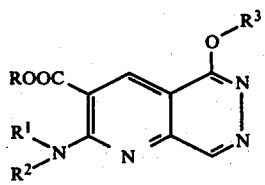

(I)

| Ex. | R | N(R¹)(R²) | R³ |
|---|---|---|---|
| 10 | C₂H₅ | —NH₂ | C₂H₅ |
| 11 | C₂H₅ | —NH—C₂H₅ | H |
| 12 | C₂H₅ | —NH—C₃H₇ | C₂H₅ |
| 13 | H | —NH—C₄H₉ | H |
| 14 | H | —N(CH₃)₂ | H |
| 15 | C₂H₅ | —N(C₂H₅)₂ | C₂H₅ |
| 16 | H | —NH—C₆H₅ | i-C₃H₇ |
| 17 | H | —NH—C₆H₄—COOH | C₂H₅ |
| 18 | CH₃ | —NH—C₆H₄—CH₃ | C₂H₅ |
| 19 | H | —NH—CH₂—C₆H₅ | CH₃ |
| 20 | C₃H₇ | —NH—CH₂CH₂N(C₂H₅)₂ | C₂H₅ |
| 21 | H | —N(CH₂—C₆H₅)₂ | C₂H₅ |
| 22 | C₂H₅ | —N(pyrrolidinyl) | C₂H₅ |
| 23 | CH₃ | —N(piperidinyl) | C₂H₅ |
| 24 | H | —N(piperazinyl)N—CH₂CH₂OH | H |
| 25 | C₂H₅ | —NHCH₂CH₂N(CH₃)₂ | H |
| 26 | H | —NHCH₃ | CH₃ |
| 27 | C₂H₅ | —N(pyridyl) | CH₃ |
| 28 | C₂H₅ | —N(3,5-dimethylpiperidinyl) | C₂H₅ |
| 29 | C₂H₅ | —N(4-methylpiperazinyl) | H |
| 30 | H | —NH—C₆H₄—CH₃ | CH₃ |
| 31 | C₂H₅ | NHCH₂CH₂—C₆H₄—CH₃ | C₂H₅ |
| 32 | H | NH(CH₂)₃N(C₂H₅)₂ | C₂H₅ |

-continued

| Ex. | R | N(R¹)(R²) | R³ |
|---|---|---|---|
| 33 | C₂H₅ | NHC₄H₉ | CH₂CH₂CH(CH₃)CH₃ |

What is claimed is:

1. A compound of the formula

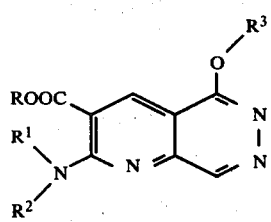

wherein R is hydrogen or lower alkyl, $R^1$ and $R^2$ each is hydrogen, lower alkyl, phenyl, substituted phenyl, wherein the phenyl substituent is one or two of the groups lower alkyl, trifluormethyl or carboxy, phenyl-lower alkylene, di-lower alkylamino-lower alkylene or the group

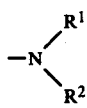

is a pyrrolidine, piperidino, pyrazolyl, pyrimidinyl, pyrazinyl, dihydropyridazinyl or piperazinyl radical each of which may bear one hydroxy-lower alkyl group or one or two lower alkyl groups, and $R^3$ is hydrogen or lower alkyl, and phsyiologically acceptable acid addition salts thereof.

2. A compound as in claim 1 wherein R and $R^3$ each is hydrogen or lower alkyl, $R^1$ is lower alkyl and $R^2$ is hydrogen.

3. A compound as in claim 1 wherein R, $R^1$, $R^2$ and $R^3$ each is ethyl.

4. A compound as in claim 1 wherein R and $R^3$ each is ethyl, $R^1$ is butyl and $R^2$ is hydrogen.

5. A compound as in claim 1 wherein R and $R^3$ each is ethyl, $R^1$ is propyl and $R^2$ is hydrogen.

6. A compound as in claim 1 wherein R and $R^1$ each is ethyl, $R^2$ and $R^3$ each is hydrogen.

7. A compound as in claim 1 wherein R and $R^1$ each is hydrogen, $R^2$ is

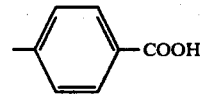

and $R^3$ is ethyl.

8. A compound of the formula

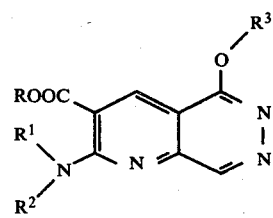

wherein R and $R^3$ each is hydrogen or lower alkyl, $R^1$ and $R^2$ each is hydrogen, lower alkyl, phenyl, substituted phenyl, wherein the phenyl substituent is one or two of the groups lower alkyl, trifluoromethyl or carboxy, phenyl-lower alkylene, or di-lower alkylamino-lower alkylene, and physiologically acceptable acid addition salts thereof.

9. A compound as in claim 8 wherein R is hydrogen or lower alkyl, $R^1$ is ethyl, propyl or butyl, $R^2$ is hydrogen and $R^3$ is hydrogen, methyl, ethyl or isopentyl.

10. A compound as in claim 8 wherein R is ethyl, $R^1$ is hydrogen, $R^2$ is butyl and $R^3$ is isopentyl.

11. A compound as in claim 8 wherein R and $R^1$ each is hydrogen, $R^2$ is butyl and $R^3$ is ethyl.

12. A compound as in claim 8 wherein $R^1$ and $R^2$ each is hydrogen and R and $R^3$ each is ethyl.

13. A compound as in claim 8 wherein R, $R^1$ and $R^3$ each is hydrogen and $R^2$ is butyl.

14. A compound as in claim 8 wherein R is ethyl, $R^1$ is butyl and $R^2$ and $R^3$ each is hydrogen.

* * * * *